US012611535B2

(12) United States Patent
Segura Ortega et al.

(10) Patent No.: US 12,611,535 B2
(45) Date of Patent: Apr. 28, 2026

(54) INTRAVASCULAR BLOOD PUMP

(71) Applicant: ABIOMED, Inc., Danvers, MA (US)

(72) Inventors: Carlos Alejandro Segura Ortega, Danvers, MA (US); Andrew Gentile, Danvers, MA (US)

(73) Assignee: ABIOMED, INC., Danvers, MA (US)

( * ) Notice: Subject to any disclaimer, the term of this patent is extended or adjusted under 35 U.S.C. 154(b) by 466 days.

(21) Appl. No.: 18/073,162

(22) Filed: Dec. 1, 2022

(65) Prior Publication Data

US 2023/0173252 A1     Jun. 8, 2023

Related U.S. Application Data

(60) Provisional application No. 63/293,241, filed on Dec. 23, 2021, provisional application No. 63/285,810, filed on Dec. 3, 2021.

(51) Int. Cl.
    *A61M 60/546*        (2021.01)
    *A61M 60/165*        (2021.01)
(52) U.S. Cl.
    CPC ........ *A61M 60/546* (2021.01); *A61M 60/165* (2021.01)
(58) Field of Classification Search
    None
    See application file for complete search history.

(56) References Cited

U.S. PATENT DOCUMENTS

| 7,640,046 | B2 * | 12/2009 | Pastore | ............... A61B 5/1107 |
| | | | | 600/478 |
| 10,646,274 | B2 * | 5/2020 | Kowalewski | .......... A61B 18/24 |
| 2004/0010192 | A1 * | 1/2004 | Benaron | .............. A61B 5/0075 |
| | | | | 600/431 |
| 2004/0071637 | A1 | 4/2004 | Elia | |

(Continued)

FOREIGN PATENT DOCUMENTS

DE        102018220658 A1      6/2020

OTHER PUBLICATIONS

International Search Report, and Written Opinion, for corresponding PCT application No. PCT/US22/51660, dated May 3, 2023.

(Continued)

*Primary Examiner* — Carl H Layno
*Assistant Examiner* — Manolis Pahakis
(74) *Attorney, Agent, or Firm* — Meagher Emanuel Laks Goldberg & Liao, LLP

(57)               ABSTRACT

Techniques and systems for using spectroscopy, and/or image-based sensing with an intravascular blood pump are provided. The techniques generally include capturing a spectral response to light of a measured tissue and/or blood. Based on the specific needs, the method may include, e.g., determining a type of the measured tissue based on the spectral response, determining if the type of the measured tissue matches a target tissue type, determining a health of the measured tissue based on the spectral response, determining a treatment plan based on the health of the measured tissue, determining a type and/or quantity of components (Continued)

and/or characteristics in the blood, and/or determining a degree of heart recovery based on the type and/or quantity of the components and/or characteristics in the blood.

17 Claims, 5 Drawing Sheets

(56)                    References Cited

U.S. PATENT DOCUMENTS

| | | | |
|---|---|---|---|
| 2005/0004453 A1* | 1/2005 | Tearney | A61B 5/416 |
| | | | 356/450 |
| 2006/0063993 A1 | 3/2006 | Yu | |
| 2008/0125634 A1* | 5/2008 | Ryan | A61B 5/145 |
| | | | 606/15 |
| 2009/0227952 A1* | 9/2009 | Blakstvedt | A61B 5/0084 |
| | | | 604/117 |
| 2009/0234445 A1* | 9/2009 | Maschke | A61B 5/02007 |
| | | | 623/2.11 |
| 2010/0022861 A1* | 1/2010 | Cinbis | A61B 5/0086 |
| | | | 600/300 |
| 2010/0069760 A1* | 3/2010 | Tang | A61B 5/02007 |
| | | | 600/478 |
| 2010/0240944 A1* | 9/2010 | Maschke | A61M 60/867 |
| | | | 600/16 |
| 2011/0212090 A1 | 9/2011 | Pedersen | |
| 2013/0109938 A1 | 5/2013 | Kuhn | |
| 2014/0270430 A1* | 9/2014 | Nair | A61B 17/22 |
| | | | 382/128 |
| 2015/0087890 A1* | 3/2015 | Spanier | A61M 60/165 |
| | | | 600/16 |
| 2015/0282747 A1* | 10/2015 | Thiele | A61B 5/14552 |
| | | | 600/327 |
| 2017/0086719 A1* | 3/2017 | Freeman | A61B 5/14539 |
| 2017/0173275 A1* | 6/2017 | Anderson | A61B 5/0084 |
| 2018/0049728 A1* | 2/2018 | Berlin | A61B 10/0283 |
| 2019/0154660 A1 | 5/2019 | Cafferty | |
| 2020/0093973 A1* | 3/2020 | Gandhi | A61M 60/818 |
| 2020/0315432 A1* | 10/2020 | Tully | H04N 23/55 |
| 2020/0367757 A1* | 11/2020 | Ting | A61B 5/0537 |
| 2020/0405930 A1* | 12/2020 | Zhang | A61M 60/216 |
| 2021/0007596 A1 | 1/2021 | Landesman et al. | |
| 2021/0038306 A1* | 2/2021 | McLoughlin | A61B 5/0084 |
| 2021/0236783 A1 | 8/2021 | Korkuch et al. | |
| 2021/0369118 A1* | 12/2021 | Sarvazyan | A61B 18/1815 |
| 2021/0386479 A1* | 12/2021 | Massimini | A61B 5/0075 |
| 2021/0396661 A1* | 12/2021 | Hendon | G01N 21/3563 |
| 2022/0095937 A1* | 3/2022 | Faircloth | A61B 5/1455 |
| 2022/0183755 A1* | 6/2022 | Finley | A61B 17/320068 |
| 2023/0144756 A1* | 5/2023 | Ship | A61B 5/02154 |
| | | | 600/17 |
| 2023/0355958 A1* | 11/2023 | Lee | A61M 60/216 |
| 2024/0402087 A1* | 12/2024 | Hancock | A61B 5/0075 |

OTHER PUBLICATIONS

The EESR for corresponding EP Application No. 22902229.8, dated Oct. 8, 2025 (9 pages).

* cited by examiner

INTRAVASCULAR BLOOD PUMP

CROSS-REFERENCE TO RELATED APPLICATIONS

The present application claims priority to U.S. Provisional Pat. Appl. Nos. 63/285,810, filed Dec. 3, 2021, and 63/293, 241, filed Dec. 23, 2021, each of which is incorporated by reference herein in its entirety.

TECHNICAL FIELD

The present disclosure relates to blood pump assemblies, such as an intravascular blood pump assembly arranged to support flow in a patient's blood vessel, and in particular to devices and methods for installing such devices and for monitoring the patient in which the devices are installed (e.g., the patient's vascular system).

BACKGROUND

Intravascular blood pumps can be introduced into a patient either surgically or percutaneously and used to deliver blood from one location in the heart or circulatory system to another location in the heart or circulatory system. For example, when deployed in the left heart, an intravascular blood pump can pump blood from the left ventricle of the heart into the aorta. Likewise, when deployed in the right heart, an intravascular blood pump can pump blood from the inferior vena cava into the pulmonary artery. Examples of such blood pumps include the Impella® family of devices (Abiomed, Inc., Danvers, MA).

Blood pumps may have one or more sensors for measuring the patient's vascular system. For example, intravascular blood pumps may include one or more optical sensors for measuring pressures within a patient's vascular system, and in particular a patient's ventricular cavity, which may be used for operating the blood pump and/or for assessing the state of the patient's heart.

BRIEF SUMMARY

In some embodiments, a method of positioning a medical device, such as an intravascular blood pump, in a patient is disclosed. In some embodiments, the method includes detecting a type of tissue at a first location via a sensor on the medical device and determining if the detected type of tissue matches a target tissue type. If the determined tissue type and target tissue type match, the method includes securing the intravascular blood pump. If the determined tissue type and the target tissue type differ, the method includes moving the medical device to a second location and performing the detecting and determining steps a second time. As will be appreciated, the medical device can be moved to third, fourth, fifth (or more) locations, with the detecting and determining steps being repeated until the target tissue type and detected tissue type match.

In some embodiments, the detector includes a spectroscopy-based sensor, and the method includes a method for spectroscopy-based sensing using an intravascular blood. The method may include capturing a spectral response to light of a measured tissue, determining a type of the measured tissue based on the spectral response, and determining if the type of the measured tissue matches a target tissue type.

In some embodiments, capturing the spectral response to light of the measured tissue may include shining light on the measured tissue via a sensor and sensing a reflected light (e.g., via a detector, such as a spectrometer or image detector). In some embodiments, the method may include adjusting a distance the intravascular blood pump has been inserted into a blood vessel of a patient and repeating the capturing and determining steps. In some embodiments, the method may include generating an indication, or otherwise indicating to a user, when the determined tissue type matches the target tissue type.

In some embodiments, the method may include determining a distance from the intravascular blood pump to the measured tissue having the target tissue type. In some embodiments, the method may include determining if the distance from the intravascular blood pump to the measured/detected tissue having the target tissue type matches a target distance between the intravascular blood pump and a patient's vasculature. In some embodiments, the method may include adjusting a position of the intravascular blood pump relative to the measured tissue having the target tissue type, and repeating the distance-determining steps until the intravascular blood pump is positioned at the prescribed distance from the target tissue. In some embodiments, the type of the measured tissue may be based on information from a first sensor, and the distance from the intravascular blood pump to the measured tissue may be based on information from a second sensor, such as from a distance sensor.

In some embodiments, the method may include determining a health of the measured tissue. In some embodiments, determining the health of the measured tissue may include classifying the health of the measured tissue into one or more categories from a list of categories (such as healthy, recovered, and injured).

In some embodiments, the method may include proposing a treatment plan based on the health of the measured tissue as determined. In some embodiments, the method may include determining the treatment plan to be proposed. In some embodiments, the treatment plan may be based on a plurality of characteristics, the plurality of characteristics including characteristics of the measured tissue and/or the blood of a patient. In some embodiments, the plurality of characteristics may include characteristics of the patient, such as characteristics of a heart of the patient. In some embodiments, the health of the measured tissue may be determined by an evaluation system. The evaluation system may include a database of spectral responses of tissues with known tissue health. In some embodiments, determining the health of the measured tissue may include comparing the spectral response of the measured tissue to a spectral response of tissues with known tissue health in the database. In some embodiments, determining the health of the measured tissue includes determining if the spectral response has a similarity to a first spectral response of a tissue with a first known tissue health above a threshold, and has a similarity to a second spectral response of a tissue with a second known tissue health above the threshold.

In some embodiments, the method may include proposing a treatment plan, wherein the treatment plan includes retesting tissue health after a period of time when the spectral response has a similarity to a first spectral response of a tissue with a first known tissue health above a threshold, and has a similarity to a second spectral response of a tissue with a second known tissue health above the threshold.

In some embodiments, the method may include capturing an additional spectral response (e.g., to light) of blood (e.g., blood in and/or around the pump) and determining a characteristic of the blood based on the additional spectral response. In some embodiments, the characteristic of the blood may include an identification or type of at least one material in the blood, and a concentration of the at least one material. In some embodiments, the characteristic of the blood may be an oxygenation of blood (which may be determined, e.g., based on a determination of an absorption, transmission, and/or reflection of the light by the blood). In some embodiments, the characteristic of the blood may be hemolysis. In some embodiments, the characteristic of the blood may be lactic acidosis. In some embodiments, the method may include generating an alert when the characteristic of the blood based on the additional spectral response has a value above (and/or below) a prescribed threshold. In some embodiments, the method may include determining a degree of heart recovery based on a plurality of characteristics of the blood based on the additional spectral response.

In some embodiments, the plurality of characteristics may include an identification or classification of at least one material in the blood, and a concentration of the at least one material. In some embodiments, the method may include determining and proposing a treatment plan based on the degree of heart recovery. In some embodiments, determining the degree of heart recovery may include comparing an identification or type and concentration of one or more materials in the blood to values from a database.

A method for using spectroscopy-based sensing with an intravascular blood pump may be provided. The method may include capturing a spectral response to light of a measured tissue (such as cardiac tissue), determining a health of the measured tissue based on the spectral response, determining a treatment plan based on the health of the measured tissue, and proposing the treatment plan. In some embodiments, determining the heath of the measured tissue may be determined by an evaluation system. In some embodiments, the method may include sensing and measuring other components and/or characteristics of the patient. In some embodiments, sensing and measuring other components and/or characteristics may include causing a light to irradiate blood in and/or around the pump, and sensing and analyzing the light after it reflects off components in the blood. In some embodiments, sensing and measuring other components and/or characteristics includes evaluating hemolysis while the pump is being used. In some embodiments, sensing and measuring other components and/or characteristics includes determining a concentration of lactic acid. In some embodiments, the method may include generating an alert if a concentration of a component in the blood, or a value of a characteristic of the blood, is determined to be above and/or below a threshold value. In some embodiments, the method may include automatically formatting and incorporating a selected treatment plan or treatment step into a medical record of a patient.

A method for determining a degree of heart recovery also may be provided. The method may include irradiating blood in and/or around an intravascular blood pump with a light, capturing a spectral response to the light, determining a type and/or quantity of components and/or characteristics in the blood, and determining a degree of heart recovery based on the type and/or quantity of the components and/or characteristics in the blood. In some embodiments, the method may include generating an alert if: the determination of heart recovery is above and/or below one or more thresholds; if the quantity of one or more components is determined to be above and/or below one or more thresholds; if the characteristics in the blood are determined to be above and/or below one or more thresholds; or a combination thereof. In some embodiments, the method may include determining and proposing a treatment plan based on the degree of heart recovery.

In still other embodiments, a system may be provided. The system may include an intravascular blood pump, a sensor disposed in or on the intravascular blood pump, the sensor being operably coupled to one or more processors, a light source, a spectrometer or image detector, and a non-transitory computer-readable storage medium. The non-transitory computer-readable storage medium may contain instructions that, when executed by the one or more processors, causes the system to: pass a light from the light source through the sensor towards a tissue to be measured within a patient's vasculature; sense, using the spectrometer or image detector, a spectral response of light of the measured tissue captured by the sensor; determine a type of the measured tissue based on the spectral response; and determine if the type of the measured tissue matches a target tissue type.

In some embodiments, the system may be configured to indicate to a user when the type matches the target tissue type. In some embodiments, the system may be configured to determine a distance (e.g., using a distance sensor) from the intravascular blood pump to the measured tissue having the target tissue type. In some embodiments, the system may be configured to determine if the distance from the intravascular blood pump to the measured tissue having the target tissue type matches a target distance. In some embodiments, the system may be configured to determine a health of the measured tissue. In some embodiments, the system may be configured to classify the health of the measured tissue into one or more categories from a list of categories (e.g., as healthy, recovered, and/or injured). In some embodiments, the system may be configured to determine and propose a treatment plan based on the health of the measured tissue as determined. In some embodiments, the treatment plan may be determined based on a plurality of characteristics, the plurality of characteristics including characteristics of the measured tissue and/or blood of a patient. In some embodiments, the plurality of characteristics may include characteristics of the patient and/or a heart of the patient.

In some embodiments, the system may include a database operably coupled to the one or more processors. In some embodiments, the system may be configured to compare the spectral response of the measured tissue to spectral response of tissues with known tissue health in the database. In some embodiments, the system may be configured to determine if the spectral response has a similarity to a first spectral response of a tissue with a first known tissue health above a threshold, and has a similarity to a second spectral response of a tissue with a second known tissue health above the threshold. In some embodiments, the system may be configured to retest tissue health after a period of time after determining that the spectral response has a similarity to a first spectral response of a tissue with a first known tissue health above a threshold, and has a similarity to a second spectral response of a tissue with a second known tissue health above the threshold. In some embodiments, the system may be configured to capture an additional spectral response (e.g., to light) of blood, and determine a characteristic of blood based on the additional spectral response. In some embodiments, the characteristic of blood may include an identification or type of at least one material in the blood, and a concentration of the at least one material. In some embodiments, the characteristic of blood may be oxygenation of blood. In some embodiments, the system may be configured to determine the oxygenation of blood based on a determination of an absorption, transmission, and/or reflection of the light by the blood. In some embodiments, the characteristic of the blood may be hemolysis. In some embodiments, the characteristic of the blood may be lactic acidosis. In some embodiments, the system may be configured to generate an alert when the characteristic of the blood based on the additional spectral response has a value below threshold.

In some embodiments, the system may be configured to determine a degree of heart recovery based on a plurality of characteristics of blood based on the additional spectral response. In some embodiments, the plurality of characteristics includes an identification or classification of at least one material in the blood, and a concentration of the at least one material. In some embodiments, the system may be configured to determine and propose a treatment plan based on the degree of heart recovery. In some embodiments, the system may be configured to determine the degree of heart recovery by comparing an identification or type and concentration of one or more materials in the blood to values from a database.

BRIEF DESCRIPTION OF DRAWINGS

The accompanying drawings, which are incorporated in and constitute a part of this specification, illustrate embodiments of the present disclosure and, together with a general description of the disclosure given above, and the detailed description of the embodiments given below, serve to explain the principles of the present disclosure.

DETAILED DESCRIPTION

Figure 1:
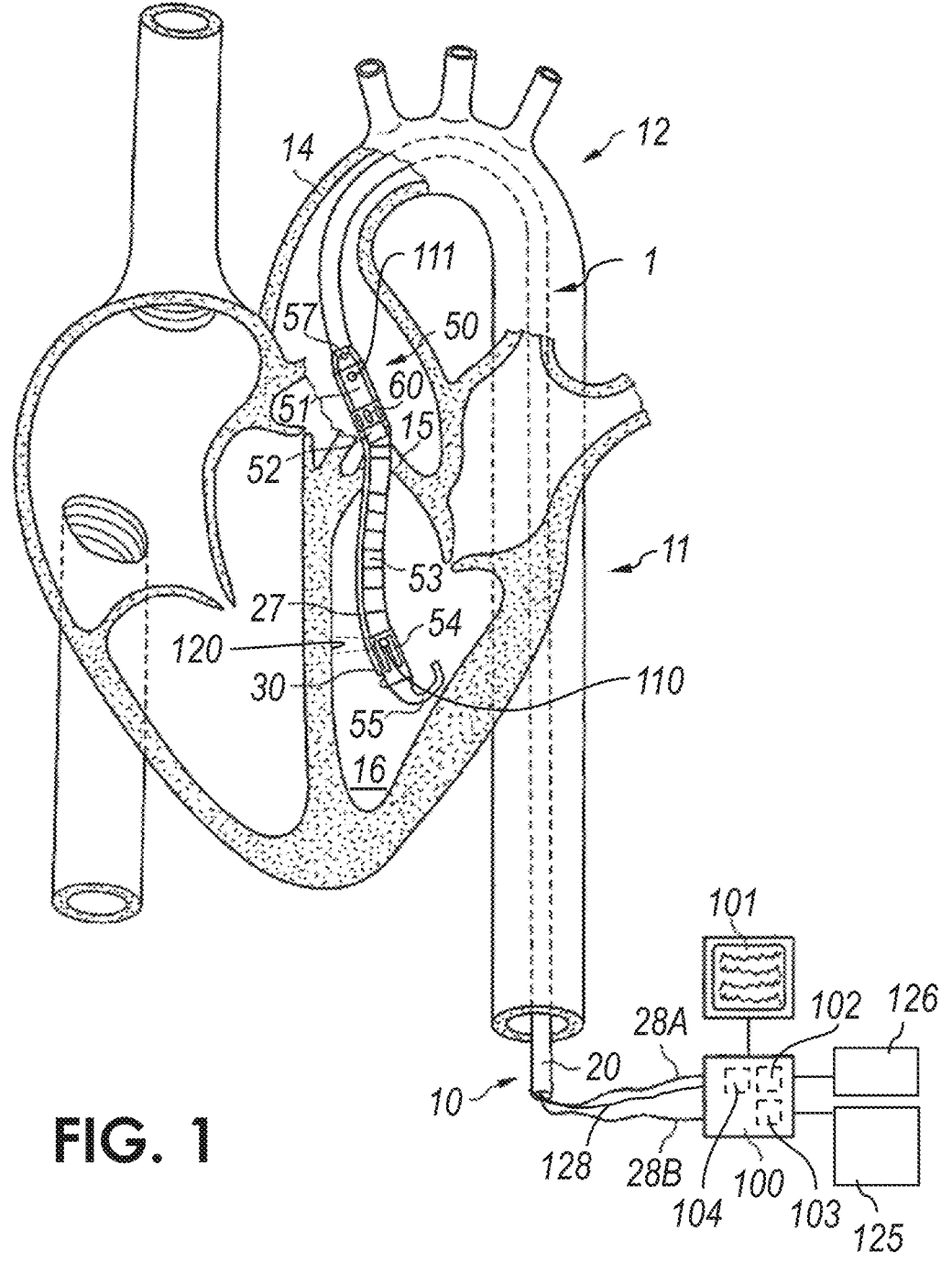
FIG. 1 is depiction of a blood pump laid through the aorta, extending through the aortic valve into the left ventricle and having an integrated pressure sensor.

The following description and drawings illustrate the principles of the present disclosure. It will thus be appreciated that those skilled in the art will be able to devise various arrangements that, although not explicitly described or shown herein, embody the principles of the disclosure and are included within its scope. Furthermore, all examples recited herein are intended to be for illustrative purposes to aid the reader in understanding the principles of the present disclosure and the concepts contributed by the inventors to furthering the art and are to be construed as being without limitation to such specifically recited examples and conditions. Additionally, the term, "or," as used herein, refers to a non-exclusive or, unless otherwise indicated (e.g., "or else" or "or in the alternative"). Also, the various embodiments described herein are not necessarily mutually exclusive, as some embodiments can be combined with one or more other embodiments to form new embodiments.

The numerous innovative teachings of the present application will be described with particular reference to the presently preferred exemplary embodiments. However, it should be understood that this class of embodiments provides only a few examples of the many advantageous uses of the innovative teachings herein. In general, statements made in the specification of the present application do not necessarily limit any of the various claimed embodiments. Moreover, some statements may apply to some inventive features but not to others. Those skilled in the art and informed by the teachings herein will realize that the disclosure is also applicable to various other technical areas or embodiments.

Various embodiments are directed to intravascular blood pumps. As is known, intravascular blood pumps can be introduced into a patient either surgically or percutaneously for delivering blood from one location in the heart or circulatory system to another location in the heart or circulatory system. For example, when deployed in the left heart, an intravascular blood pump can pump blood from the left ventricle of the heart into the aorta. Likewise, when deployed in the right heart, an intravascular blood pump can pump blood from the inferior vena cava into the pulmonary artery. In some instances, such blood pumps may have one or more sensors, such as for monitoring the patient (e.g., the patient's vascular system).

As described herein, the inventors have appreciated the benefit of a medical device, such as the disclosed percutaneous heart pump, having one or more sensors used to measure types and characteristics of certain types of tissues in the body. For example, in some embodiments herein, an intravascular blood pump may include one or more sensor (e.g., one or more spectroscopy-based sensors) configured to detect and to differentiate between different types of tissue at or near the intravascular blood pump. In some embodiments, spectroscopy-based sensing may be used to differentiate between different types of tissue in and around the heart to characterize such tissue. In some embodiments, the sensors may include optical sensors, such as a biophotonic sensors. In some embodiments, the method of elastic scattering spectroscopy may be used to discriminate between various types of tissues.

According to one aspect herein, the disclosed sensors (e.g., spectroscopy-based sensors) may be used to appropriately position an intravascular blood pump in the heart. For example, the one or more sensors may be used to determine the different types of tissue around the sensor and pump— e.g., tissue in and around the heart (e.g., the aorta, the heart wall, valves, veins, etc.)— such that a clinician may determine the appropriate position of the pump relative to a desired tissue type as the percutaneous blood pump is being installed in a patient. In one such example, the sensor may be used to differentiate between the vein tissue, artery, and heart tissues, until the pump is positioned at or near the desired type of tissue. In some embodiments, sensed data from the one or more sensors (e.g., spectroscopy-based sensors) may be used to determine proximity and/or contact with different tissues in and or around the heart (e.g., aorta, veins, heart walls) to determine the appropriate position of the pump in the heart.

As will be appreciated, although spectroscopy-based sensing has been disclosed for sensing and/or determining a desired type and/or proximity of the tissue at or near the blood pump or sensor to appropriately position the blood pump in a patient's heart, other suitable sensors may be used in other embodiments.

In some embodiments, the sensed data may be used alone or in combination with data retrieved from one or more other sensors to appropriately position the pump in the heart. For example, sensed data from the tissue sensor (e.g., spectroscopy-based sensor) may be combined with proximity data sensed from another sensors (e.g., indicating the distance between the pump and any surrounding tissue) to determine the appropriate distance between the desired tissue and the pump.

According to another aspect of the present disclosure, systems and methods may use spectroscopy-based sensing (or other suitable sensors) to assess and track heart recovery. For example, such sensors may be used to assess and track the progression of heart healing of cardiac tissue over time. In some embodiments, such sensors may be used to determine an appropriate duration of therapy and/or support with an intravascular blood pump. For example, in some embodiments, the spectroscopy-based sensors may be used to determine the state of cardiac tissue at the start of therapy and during support (e.g., at different times during support). In some embodiments, when the state of the heart tissue has reached a threshold of cardiac tissue indicating recovered cardiac tissue, the sensed data may be used to suggest weaning off support with the cardiac pump.

As will be appreciated, in some embodiments, machine learning may be used to determine both the type and state of different tissues in and around the heart. For example, in some embodiments, the sensors may be configured to sense various types of known tissue samples (e.g., aorta, veins, cardiac walls) and/or different stages of cardiac tissue, such that a knowledge base of samples may be obtained. In such embodiments, the sensed data may include a spectral response to light.

According to another aspect, spectroscopy-based sensing may be used to assess and track heart recovery by measuring blood chemistry. For example, in some embodiments, the spectroscopy-based sensors may be arranged to measure one or more components (e.g., lactic acid, red blood cells, and/or anticoagulation agents) and/or one or more characteristics of the blood (e.g., oxygenation and/or hemolysis). In such embodiments, the level of the one or more blood components and/or characteristics of such components may be used to determine the degree of heart recovery. For example, in one embodiment, the levels may be used to infer and/or detect muscle fatigue, which may then be used to evaluate the degree of heart recovery.

Turning now to the figures, FIG. 1 shows an exemplary intravascular blood pump 1 having a catheter 10 which may be introduced into a patient's heart. For example, as show in this figure, the pump may be inserted into the descending aorta 11 retrograde in some embodiments. As is known, the descending aorta is part of the aorta 12 which first ascends from the heart and then descends and has the aortic arch 14. At the beginning of the aorta 12 there is located the aortic valve 15 which connects the left ventricle 16 to the aorta 12 and through which the intravascular blood pump may extend.

As will be appreciated, blood pumps may be inserted into other suitable portions of the body. For example, in some embodiments, a blood pump may be inserted into a right ventricle. In some embodiments, a blood pump may be inserted into a femoral artery or a jugular vein.

As shown in FIG. 1, the intravascular blood pump 1 may include a rotary pumping device 50 fastened at the distal end of the catheter hose 20 and having a pump section 52 (sometimes referred to herein as simply "pump") disposed at an axial distance therefrom. In some embodiments, the blood pump may include a motor section 51 operable coupled to the pump section. In some embodiments, the motor section may be positioned distally from the distal end of the catheter hose. In some embodiments, the motor section may be position proximally from the catheter hose, and may be coupled to the pump section via a flexible drive shaft.

The intravascular blood pump may include a cannula 53 (which may be a flexible flow cannula) protruding in the distal direction from the inflow end of the pump section 52 and having a suction inlet 54 located at its end. Distally of the suction inlet 54 there may be provided a soft-flexible tip 55, which can be configured for example as a "pigtail" or in a J shape. Through the catheter hose 20 there extend different lines and devices which may be important for operating the pumping device 50.

In some embodiments, the pump may include optical fibers 28A, 28B that are attached at their proximal end to an evaluation device 100. These optical fibers 28A, 28B may be respectively part of an optical sensor (such as a pressure sensor) whose sensor heads 30 and 60 may be located in the vicinity of the suction inlet 54, on the one hand, and on the outside on the housing of the pump section 52, on the other hand. FIG. 1 shows sensor head 30 as being on the outside of the blood pump, but the sensor head could also be located internal to the blood pump, preferably within an inflow cage, the inflow cage having lumens therethrough that define the suction inlet 54. In such embodiments, information (e.g., pressure information) may be transmitted by the sensor heads 30 and 60 to the evaluation device 100 and may be converted into electrical signals in the evaluation device 100 and displayed e.g., on a display screen 101.

As also shown in FIG. 1, the pump may include a sensor 110, such as a sensor arranged for spectroscopy-based sensing, as described herein. As shown in this figure, the sensor 110 may be placed on the inlet 52 housing in some embodiments. The sensor also may be positioned on other suitable portions of the pump, such as on the flexible tip 55, the cannula 53, and/or on the outlet 60 housing. As will be appreciated, in some embodiments, the pump may include only a single sensor (e.g., a spectroscopy-based sensor). However, in other embodiments, the pump may include more than one such sensor (e.g., both the sensor 110 as well as an additional sensor 111 arranged for spectroscopy-based sensing. If a plurality of sensors are used, two or more of the sensors may be located at the same portion of the pump (e.g., on the inlet housing) and/or on different portions of the pump (e.g., on the flexible tip and the inlet housing).

In some embodiments, light (e.g., white light) may be directed at a section of tissue 120 via the sensor, with reflected light from the tissue being detected by the sensor and then analyzed by a detector 125, such as a spectrometer or image detector. A light source 126, which may be separate or may be part of the spectrometer or image detector, may be coupled to the evaluation device. As will be understood, the detected and measured intensities and wavelengths of the reflected light may correlate to the compositions and textures of the surfaces upon which they reflect from.

As also shown in FIG. 1, one or more fibers (e.g., first fiber 128) may extend between the sensor 110 and the evaluation device 100. In such embodiment, the fiber optics may enable the spectroscopy sensing (e.g., by transmitting the reflected light to a spectrometer or image detector). For example, in some embodiments, the distal end may include open facets to point into tissue and the proximal end may interface with a spectrometer.

Figure 2:
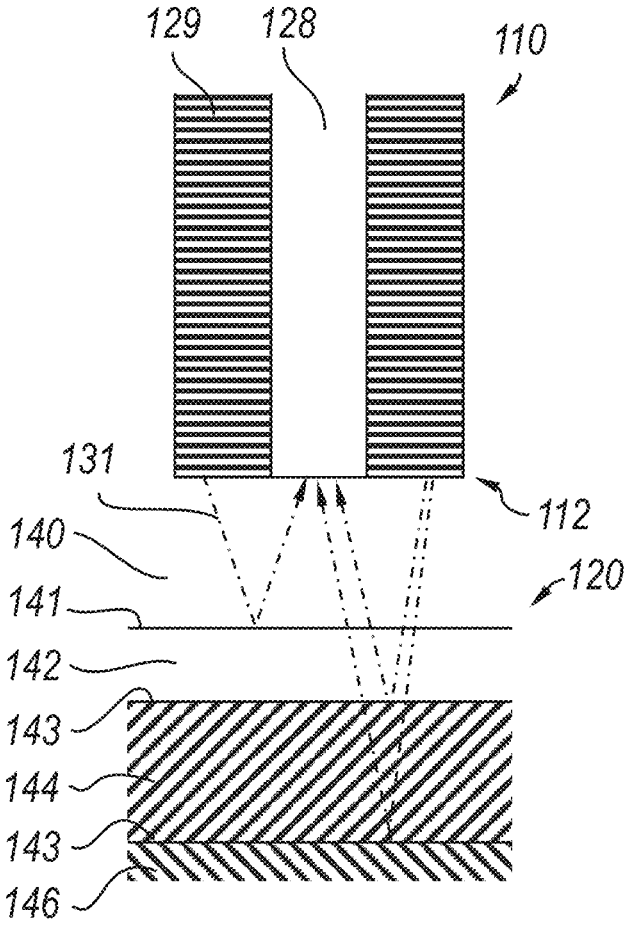
FIG. 2 is cross-sectional side view of an embodiments of a sensor interacting with tissue.

Referring to FIG. 2, in some embodiments, one or more fibers (e.g., first fiber 128) may be operably connected to the spectrometer or image detector, and one or more other fibers (e.g., second fiber 129) may be operably connected to the light source. In some embodiments, a single first fiber is connected to the spectrometer or image detector, and a plurality of second fibers are connected to the light source. A distal end 112 of each fiber may be directed towards a section of tissue 120, such that light 131 from the second fiber(s) can be directed towards the tissue, with at least some of the light the reflecting off a surface of the tissue. In some embodiments, one or more wavelengths of light (such as one or more visible wavelengths of light (generally around 400 nm-around 700 nm) and/or one or more infrared wavelength of light (generally around 700 nm-1 mm)) may reflect off a surface 141 of a first layer 142 of the tissue facing the sensor (which may be understood as the blood-tissue interface). In some embodiments, one or more wavelengths of light may transmit through the first layer and reflect off a surface 143 of a second layer 144 of the tissue facing the sensor (which may be understood as the first layer-second layer interface), where the first layer is between the second layer and the sensor. In some embodiments, one or more wavelengths may transmit through the first and second layers, and reflect off a surface 145 of a third layer 146 of the tissue facing the sensor (which may be understood as the second layer-third layer interface), where the first and second layers are between the third layer and the sensor. Depending on the power, wavelengths, etc., the light may continue transmitting through additional layers beyond the third layer, and may reflect off of a surface beyond the third layer. Note that in some embodiments, the light may be transmitted through a bodily fluid 140, such as blood, before interacting with the tissue.

After reflecting off a surface, at least some of the light transmitted from the light source enters the distal end of the first fiber and is then transmitted to the detector (e.g., spectrometer or image detector).

The detector can then determine spectral characteristics of the sample. The detector may determine, e.g., a transmission and/or reflectance of the sample. The detector may determine an absorbance of the sample.

As used herein, "spectral characteristics" may include such properties as broadband spectral profiles, peaks, and absorption bands in the spectrum, and may include temporal properties. In some embodiments, spectral characteristics of the sample may be used to determine the types and characteristics of the sample. Referring to FIG. 1, in some embodiments, one or more processors 102 coupled to the evaluation device may be used to perform the necessary analyses. As will be understood by those of skill in the art, the processor(s) may be coupled to various other components 103, 104, such as memory, non-transitory computer-readable storage medium, a wired or wireless interface, etc., as needed to perform various functions.

In some embodiments, the types and characteristics of the sample may be determined by comparing the spectral values or other spectral characteristics to those in a knowledge bank of known tissues and tissue characteristics, which may be present on a database coupled to the evaluation device. In some embodiments, a trained machine learning (ML) model may be used to classify the spectral characteristics, thereby determining the type and characteristics of the sample. For example, the spectrometer or image detector may send the processor(s) a spectral profile of the sample, after which features of the profile may be extracted, and the trained ML model may be used to determine the type and characteristics of the sample based on the extracted features.

In some embodiments, the type may include a simple binary determination of a particular desired type of tissue (e.g., whether the tissue sample is or is not cardiac tissue). In some embodiments, the type may include a determination related to a category or location of blood vessel the sensor is detecting (e.g., heart, artery, vein, etc.). In some embodiments, the characteristics may include one or more detected materials and/or one or more concentrations of the detected material(s). In some embodiments, the characteristics may include whether what is detected is healthy tissue, recovered tissue, or injured tissue.

In some embodiments, rather than being concerned with the tissue, the sensor may irradiate/shine light (e.g., white light, which typically includes wavelengths from ~380 nm to ~750 nm), which may include infrared (IR, which typically includes wavelengths from ~750 nm to ~1 mm) light, such as near-infrared (NIR, which typically includes wavelengths from ~750 nm to ~1.4 μm) light, at the blood in and/or around the pump. For example, light may illuminate the blood in the vasculature (e.g., in the ventricle) within which the pump is disposed. As disclosed herein, transmitted and/or reflected light may be sensed and analyzed by a detector, such as a spectrometer or image detector. In some embodiments, the sensed data may be used to determine the type and amount of components in and/or characteristics of the blood. In some embodiments, this information may be used to determine a degree of heart recovery.

Figure 3:
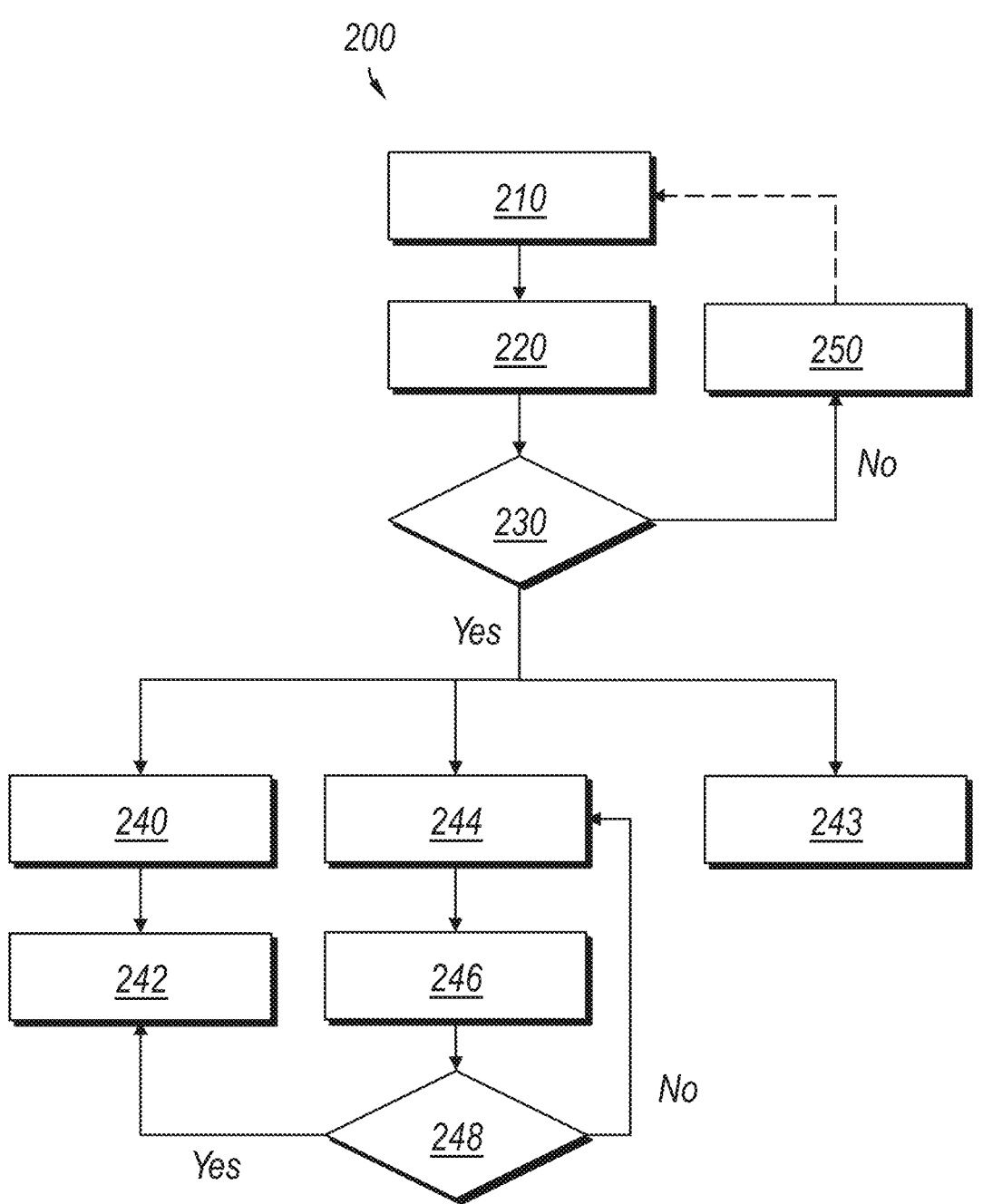
FIG. 3 is a flowchart of an embodiment of a disclosed method.

A method of using the spectroscopy-based sensing with the pump may be provided. FIG. 3 provides a flowchart showing an embodiment of such a method. As shown in this view, the method 200 may include capturing 210 a first tissue's spectral response to light. In some embodiments, this may include shining light on the first tissue via the sensor and sensing the transmitted and/or reflected light (e.g., via a spectrometer or image detector).

The transmitted and/or reflected light (e.g., sensed data) may then be analyzed to determine 220 a type of the first tissue. As disclosed herein, in some embodiments, this may be done by comparing sensed data to data stored in a database. As disclosed herein, in some embodiments, this may be done by extracting features from the sensed data and allowing a trained machine learning (ML) model to provide a determination.

The first tissue type may then be compared 230 to a desired/target tissue type. For purposes herein, the desired tissue type may include the tissue type of a desired location of the pump in the body. In that regard, the determined tissue type of the first tissue may be used to determine the location of the pump in and around the heart. For example, referring briefly to FIG. 1, in some embodiments, sensed data from a first sensor (e.g., sensor 110) may be used to determine if an inlet to the blood pump is positioned within the left ventricle (e.g., if its sensed data is indicative of cardiac tissue) and sensed data from a second sensor (e.g., additional sensor 111) may be used to determine if an outlet is in the aorta (e.g., if its sensed data is indicative of aortic tissue).

In some embodiments, the frequency of the capturing 210, determining 220, and comparing 230 steps may be 1 Hz or greater. That is, the system may capture spectral responses from transmitted light, determine the type of tissue, and compare to a desired tissue type in 1 second or less. In some embodiments, the frequency may be 1-60 Hz. In some embodiments, these steps may be done automatically while the device is being inserted. In some embodiments, these steps may be done when (or while) a clinician manually requests it (e.g., by pressing a button or switch, etc.). In still other embodiments, the frequency of capturing may include a timed step (e.g., every 1 second, 3 seconds, 5 seconds, 30 seconds, etc.).

In some embodiments, if the determined tissue type of the first tissue matches that of the desired tissue type, the method may include generating 243 an alert. In some embodiments, the alert may indicate the pump is in position. In some embodiments, the alert may indicate the clinician inserting the pump should be aware of a change. For example, referring to FIG. 1, as the blood pump is inserted into a patient, it may pass through the aortic valve and into the left ventricle. Once cardiac tissue is first detected, an alert may be generated which lets a clinician know the blood pump is almost in position. Or, in a different example, if the system is configured to discriminate the aortic arch from the descending aorta, the alert may be used to make the clinician aware the pump is getting close to the aortic valve (and placement in the heart).

In some embodiments, if the determined tissue type of the first tissue matches that of the desired tissue type (e.g., the tissue type of the desired location of the pump), the method may include having the clinician stop 240 adjusting the position of the pump. In some embodiments, such a step may be in response to an alert to the clinician that the clinician stop advancing the pump. The clinician may then secure 242 the pump in place.

In some embodiments, even if the desired tissue type of the first tissue matches that of the determined tissue type, the clinician may still adjust the position of the pump in the heart. For example, the pump also may include one or more proximity sensors (such as one of the sensors 30, 60), which may be, e.g., distance sensors. As will be appreciated, any appropriate distance sensor may be used in other embodiments. For example, the distance sensor may be an IR distance sensor. The distance sensor also may be an ultrasonic distance sensor, a laser distance sensor (e.g., a LiDAR sensor and/or an LED time-of-flight (TOF) sensor.

The proximity sensors may be used to determine 244 the position of the pump relative to the desired tissue type. In such embodiments, the clinician may adjust/move 246 the pump until it is determined 248 that the desired tissue type and proximity of the pump to the desired tissue type has been met, after which time the pump may be secured 242 in place.

In some embodiments, the frequency of updates determining the position may be 1 Hz or greater. In some embodiments, the frequency may be 1-60 Hz. The frequency also may be time based. In some embodiments, these steps may be done automatically while the device is being inserted. In some embodiments, these steps may be done when (or while) a clinician manually requests it (e.g., by pressing a button or switch, etc.).

If the determined tissue type does not match that of the desired location of the pump, the clinician may adjust the location of the pump in the body 250 (e.g., in and around the heart). As with the above, with the clinician may be provided with alerts to alert them that the pump is at or near the desired location.

As will be appreciated, the sensing and adjusting process may be repeated several (or more) times until the determined tissue type matches that of the desired tissue type (see the dashed lines in FIG. 3). In this regard, the sensor may then capture a spectral response to light of a second tissue, compare the tissue type of the second tissue to that of the desired tissue type. The pump may then be moved (or not moved) depending upon whether the second tissue type is that of the desired tissue type. As with the above, the clinician may still move the pump after reaching the desired tissue type, such as if until a desired proximity is reached to the tissue (e.g., by using one or more proximity sensors).

Figure 4:
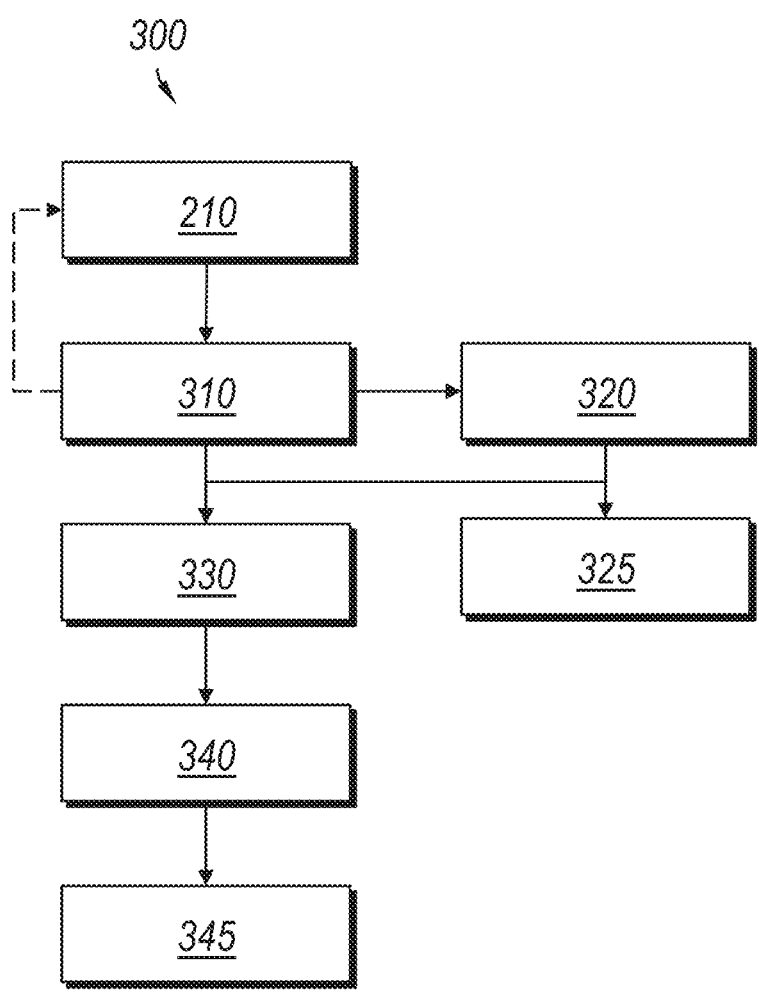
FIG. 4 is a flowchart of another embodiment of a disclosed method.

FIG. 4 shows another method of using spectroscopy-based sensing with the pump. As shown in this view, the method 300 may include capturing 210 a spectral response to light of a measured tissue. In some embodiments, the tissue is cardiac tissue.

Next, the method may include determining 310 a health of the tissue based on the spectral response. In some embodiments, this may include determining whether the tissue is healthy tissue, recovered tissue, or injured tissue. In some embodiments, the evaluation system may include a database of spectral responses of tissues with known tissue health (e.g., healthy, recovered, and injured tissue). In such embodiments, the step of determining the tissue health may include comparing the spectral response of the measured tissue to that of known tissues in the database of that tissue type. The method also may include extracting features from the spectral response and feeding the extracted features to a trained ML model to classify the tissue health of the measured tissue.

As described above, spectroscopy-based sensing methods may include sensing and measuring 320 other components and/or characteristics of the patient. For example, in some embodiments, light may be directed at the blood in and around the pump, with the transmitted and/or reflected light being sensed and analyzed (e.g., via a spectrometer or image detector). In such embodiments, the spectral readings may be used to determine the type and amount (e.g., a concentration, an absolute quantity, a relative quantity, etc.) of certain components and/or characteristics of blood. In one embodiment, the sensors may be configured to determine oxygenation of the blood (e.g., by looking and comparing absorption, transmission, and/or reflectance of light of the oxygenated versus non-oxygenated blood). In some embodiments, it is based solely on compared absorptions. In some embodiments, it is based solely on compared transmissions. In some embodiments, it is based solely on compared reflectances.

The sensors also may be used to evaluate hemolysis while the pump is being used. For example, in some embodiments, the sensors may be able to detect the spectral response of destroyed red blood cells. For example, in some embodiments, the spectral response may contain one or more features indicative of whole red blood cells, and one or more features indicative of destroyed red blood cells. In some embodiments, the fiber optic sensors may be configured to use Raman spectroscopy to provide information on chemical composition of the blood.

In some embodiments, the sensors capture one or more spectral readings at or before the time at which the pump begins to rotate, and the evaluation device compares spectral readings captured after the pump begins to rotate to the initial reading(s) to determine if there has been any change. In this way, the method may provide absolute and/or relative changes to the blood.

In still other embodiments, the sensors may be configured to measure one or more components that may be indicative of muscle fatigue, such as lactic acid.

As will be appreciated, depending upon the sensed data, the evaluation system and/or display may be arranged to provide 325 an alert (e.g., to the clinician) if certain values reach (or drop below) a predetermined threshold value.

In some embodiments, the method may include determining 330 a treatment plan, based on, e.g., the determined health of the tissue. Such determinations may be made by one or more processors, and may be made by an evaluation system, which may include a trained ML model.

In some embodiments, the treatment plan may be based on other characteristics of the tissue and/or blood. For example, in some embodiments, the treatment plan may be determined based on the determined health of the tissue, as well as concentrations of certain materials (e.g., lactic acid, etc.) in the blood, and/or a degree to which the spectral response matches a spectral response of "perfect" or "healthy" tissue. As will be further appreciated, even though the tissue may be determined to be recovered tissue, other characteristics of the patient (e.g., age, weight, BMI, etc.) and/or heart (e.g., pulse rate, blood pressure in the left ventricle, etc.) may suggest that treatment be continued.

For example, if the tissue is determined to be recovered tissue, the evaluation system may suggest that a clinician consider weaning the patient off the pump. As will be appreciated, if the determined characteristic of the tissue were determined to be injured, the system may suggest maintaining patient support with the pump.

In some embodiments, the method may include proposing 340 the determined treatment plan, such as to a clinician, via, e.g., a display. The clinician may the accept or rejected the proposed plan. In some embodiments, multiple treatment plans may be proposed, and the clinician may select a plan. In some embodiments, specific treatment steps may be proposed, and the clinician may select one or more treatment steps.

In some embodiments, the accepted treatment plan and/or treatment steps may then be automatically formatted and incorporated 345 into the medical records of the patient, which may be stored on one or more databases to which the evaluation device is operably coupled.

Although the above is described as tissues having a single defined tissue health, it will be appreciated that the tested cardiac tissue may have spectral responses that correspond to more than one tissue health (e.g., both recovered and injured). As with the above, in instances in which the spectral response corresponds to tissue having more than one tissue health, the evaluation system may be configured to propose a treatment plan of retesting after a certain period to check again for the tissue health, or may be configured to automatically retest after a certain period.

Figure 5:
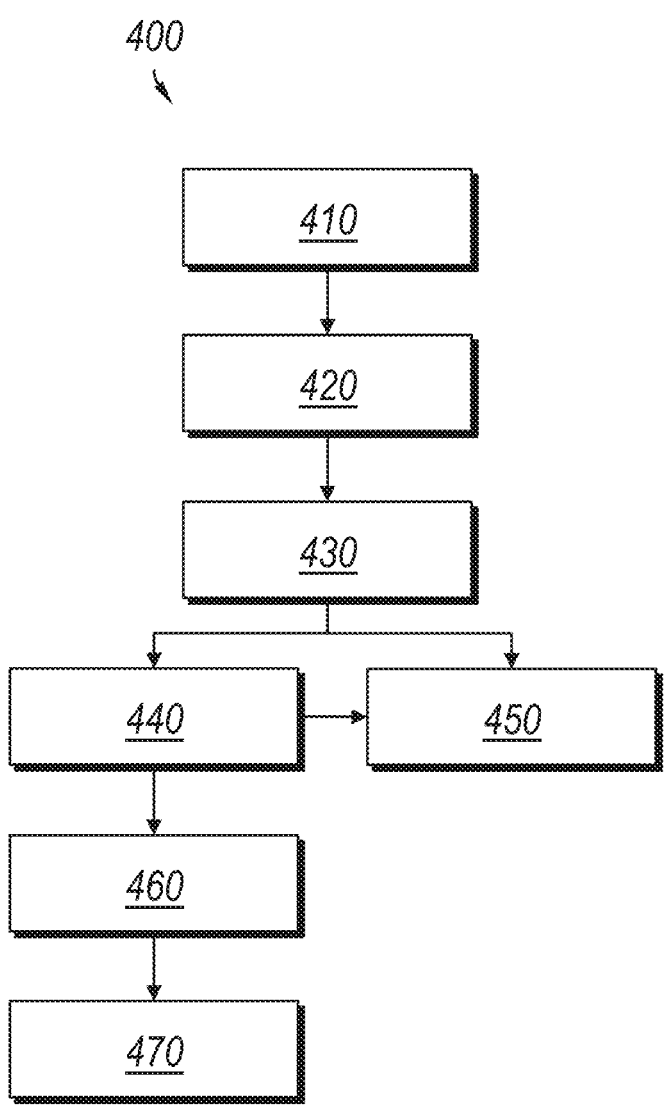
FIG. 5 is a flow chart of another embodiment of a disclosed method.

FIG. 5 illustrates a method in which such measurements may be used to determine degree of heart recovery and propose at treatment plan. For example, as shown in this view, the method 400 may include irradiating 410 blood in/around the pump with a light (e.g., a light as disclosed herein, that may be in visible wavelengths, NIR wavelengths, etc.) and capturing 420 a spectral response to the light.

The method may include determining 430 a type and/or quantity of components and/or characteristics in the blood as disclosed herein. In some embodiments, the determinations may be based on the spectral response(s). For example, determining a concentration of a specific component, degree of hemolysis, and/or blood oxygenation based on the spectral responses (e.g., by comparing to profiles in a database and/or using a trained ML model to make such determinations). In some embodiments, one or more determinations may be made based on data received from other sensors (e.g., a pressure sensor, a pH sensor, a distance sensor, etc.)

The method also may include determining 440 a degree of heart recovery based on the components and/or characteristics. For example, this may include determining a degree of heart recovery based on blood chemistry (e.g., based on the presence/or amount quantity of certain components, such as chemicals, in the blood).

The method also may include generating 450 an alert if certain conditions are met. In some embodiments, an alert may be generated if the determination of heart recovery is above (and/or below) one or more thresholds. In some embodiments, an alert may be generated if the quantity of one or more components is determined to be above (and/or below) one or more thresholds. In some embodiments, an alert may be generated if the characteristics in the blood are determined to be above (and/or below) one or more thresholds.

Finally, the method may include determining 460 and proposing 470 a treatment plan. Such plans, as disclosed herein, may be determined via an evaluation system. The determinations may depend upon the degree of heart recovery. In an illustrative embodiment, the method may include shining light at the blood via the spectroscopy-based sensor, capturing and analyzing the spectral response to light, determining the amount of lactic in the blood, inferring a degree of heart recovery based on the amount of lactic acid in the blood, and proposing a treatment plan, such as weaning the patient off the heart pump if the level of lactic acid corresponds to that of a recovered heart.

As will be appreciated, in some embodiments, the evaluation system may include a database which includes different stages of heart recovery, and the levels of different components that may correspond to each stage. In some embodiments, determining a stage of heart recovery may include comparing the type and quantity of various components in the blood to those in the database. In some embodiments, there may be two stages (e.g., injured and recovered). In other embodiments, there may be three or more stages, which may be based on different endpoints. For example, in one embodiment, the stages may use a recovery endpoint (e.g., major injury, moderate injury, minor injury, and recovered), while in another embodiment, the stages may use a surgical endpoint (e.g., immediate post-surgery, short-term recovery period, long-term recovery period, post-recovery). In some embodiments these levels may correspond to different levels of muscle fatigue, which may correspond to the different stages of heart recovery. In some embodiments, a trained ML model can be used to determine a stage of heart recovery based on extracted features from received sensor data. Depending upon the determined level, the evaluation system may propose a treatment plan.

Embodiments of the present disclosure are described in detail with reference to the figures wherein like reference numerals identify similar or identical elements. It is to be understood that the disclosed embodiments are merely examples of the disclosure, which may be embodied in various forms. Well known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

What is claimed is:

1. A system, comprising:

an intravascular blood pump;

a sensor disposed in or on the intravascular blood pump, the sensor being operably coupled to one or more processors, a light source, and a spectrometer;

a non-transitory computer-readable storage medium containing instructions that, when executed by the one or more processors, causes the system to:

pass a light from the light source through the sensor towards a tissue to be measured within a patient's vasculature;

sense, using the spectrometer, a spectral response of light of the measured tissue captured by the sensor;

determine a type of the measured tissue based on the spectral response;

determine if the type of the measured tissue matches a target tissue type;

indicate to a user when the type matches the target tissue type;

determine a distance from the intravascular blood pump to the measured tissue having the target tissue type; and determine if the distance from the intravascular blood pump to the measured tissue having the target tissue type matches a target distance.

2. The system according to claim 1, further comprising a distance sensor.

3. The system according to claim 1, wherein the system includes further instructions that, when executed by the one or more processors, causes the system to determine a health of the measured tissue.

4. The system according to claim 3, wherein the system includes further instructions that, when executed by the one or more processors, causes the system to classify the health of the measured tissue into one or more categories from a list of categories.

5. The system according to claim 4, wherein the list of categories comprises healthy, recovered, and injured.

6. The system according to claim 3, wherein the system includes further instructions that, when executed by the one or more processors, causes the system to determine and propose a treatment plan based on the health of the measured tissue as determined.

7. The system according to claim 6, where the treatment plan is determined based on a plurality of characteristics, the plurality of characteristics including characteristics of the measured tissue and/or blood of a patient.

8. The system according to claim 7, wherein the plurality of characteristics includes characteristics of the patient and/or a heart of the patient.

9. The system according to claim 6, wherein the system includes further instructions that, when executed by the one or more processors, causes the system to compare the spectral response of the measured tissue to spectral responses of tissues with known tissue health in a database.

10. The system according to claim 6, wherein the system includes further instructions that, when executed by the one or more processors, causes the system to determine if the spectral response has a similarity to a first spectral response of a tissue with a first known tissue health above a threshold, and has a similarity to a second spectral response of a tissue with a second known tissue health above the threshold.

11. The system according to claim 10, wherein the system includes further instructions that, when executed by the one or more processors, causes the system to retest tissue health after a period of time after a determining that the spectral response has a similarity to a first spectral response of a tissue with a first known tissue health above a threshold, and has a similarity to a second spectral response of a tissue with a second known tissue health above the threshold.

12. The system according to claim 1, wherein the system includes further instructions that, when executed by the one or more processors, causes the system to capture an additional spectral response to light associated with blood, and determine a characteristic of the blood based on the additional spectral response.

13. The system according to claim 12, wherein the characteristic of the blood includes an identification or type of at least one material in the blood, and a concentration of the at least one material.

14. The system according to claim 12, wherein the characteristic of the blood is oxygenation of blood.

15. The system according to claim 12, wherein the system includes further instructions that, when executed by the one or more processors, causes the system to determine a degree of heart recovery based on a plurality of characteristics of the blood based on the additional spectral response.

16. A system, comprising:

an intravascular blood pump;

a sensor disposed in or on the intravascular blood pump, the sensor being operably coupled to one or more processors, a light source, and a spectrometer;

a non-transitory computer-readable storage medium containing instructions that, when executed by the one or more processors, causes the system to:

pass a light from the light source through the sensor towards a tissue to be measured within a patient's vasculature;

sense, using the spectrometer, a spectral response of light of the measured tissue captured by the sensor;

determine a type of the measured tissue based on the spectral response;

determine if the type of the measured tissue matches a target tissue type;

determine a health of the measured tissue; and determine and propose a treatment plan based on the health of the measured tissue as determined.

17. A system, comprising:

an intravascular blood pump;

a sensor disposed in or on the intravascular blood pump, the sensor being operably coupled to one or more processors, a light source, and a spectrometer;

a non-transitory computer-readable storage medium containing instructions that, when executed by the one or more processors, causes the system to:

pass a light from the light source through the sensor towards a tissue to be measured within a patient's vasculature;

sense, using the spectrometer, a spectral response of light of the measured tissue captured by the sensor;

determine a type of the measured tissue based on the spectral response;

determine if the type of the measured tissue matches a target tissue type;

capture an additional spectral response to light associated with blood, and determine a characteristic of the blood based on the additional spectral response; and determine a degree of heart recovery based on a plurality of characteristics of the blood based on the additional spectral response.

* * * * *